(12) United States Patent
Swierkowski

(10) Patent No.: US 6,716,328 B1
(45) Date of Patent: Apr. 6, 2004

(54) MICROCHANNEL CROSS LOAD ARRAY WITH DENSE PARALLEL INPUT

(75) Inventor: Stefan P. Swierkowski, Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/538,354

(22) Filed: Mar. 29, 2000

(51) Int. Cl.[7] .......................... G01N 27/453; B01L 3/02
(52) U.S. Cl. ...................................... 204/601; 422/100
(58) Field of Search ........................... 204/600, 601; 422/100

(56) References Cited

U.S. PATENT DOCUMENTS

| | | | |
|---|---|---|---|
| 5,726,404 A | 3/1998 | Brody | 200/81 R |
| 5,795,788 A | 8/1998 | Bevan et al. | 436/161 |
| 5,846,396 A * | 12/1998 | Zanzucchi et al. | 204/601 |
| 5,900,130 A | 5/1999 | Benvegnu et al. | 204/453 |
| 6,143,152 A * | 11/2000 | Simpson et al. | 204/451 |

* cited by examiner

*Primary Examiner*—Alex Noguerola
(74) *Attorney, Agent, or Firm*—Michael C. Staggs; Alan H. Thompson

(57) ABSTRACT

An architecture or layout for microchannel arrays using T or Cross (+) loading for electrophoresis or other injection and separation chemistry that are performed in microfluidic configurations. This architecture enables a very dense layout of arrays of functionally identical shaped channels and it also solves the problem of simultaneously enabling efficient parallel shapes and biasing of the input wells, waste wells, and bias wells at the input end of the separation columns. One T load architecture uses circular holes with common rows, but not columns, which allows the flow paths for each channel to be identical in shape, using multiple mirror image pieces. Another T load architecture enables the access hole array to be formed on a biaxial, collinear grid suitable for EDM micromachining (square holes), with common rows and columns.

43 Claims, 3 Drawing Sheets

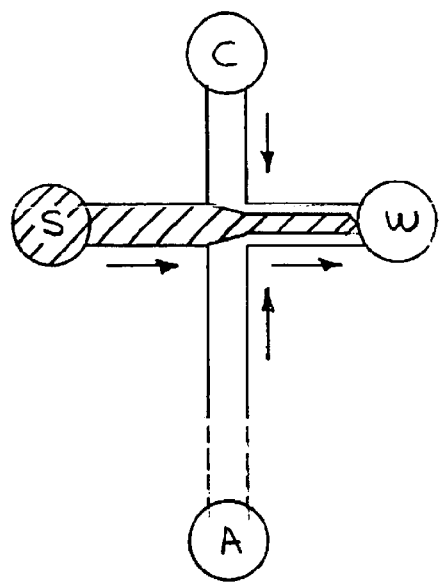
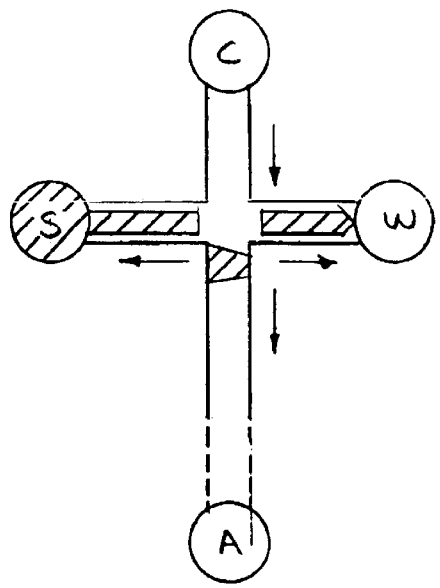
FIG. 1A (PRIOR ART)     FIG. 1B (PRIOR ART)
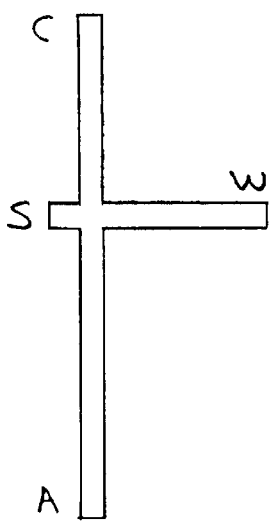
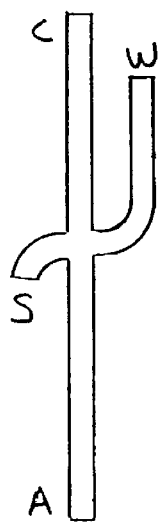
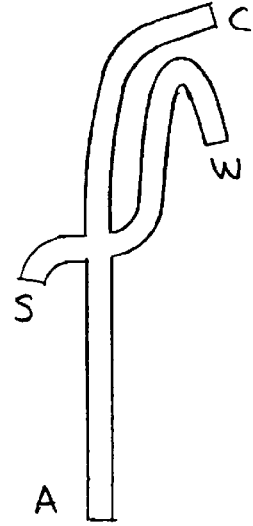
FIG. 2A     FIG 2B     FIG 2C

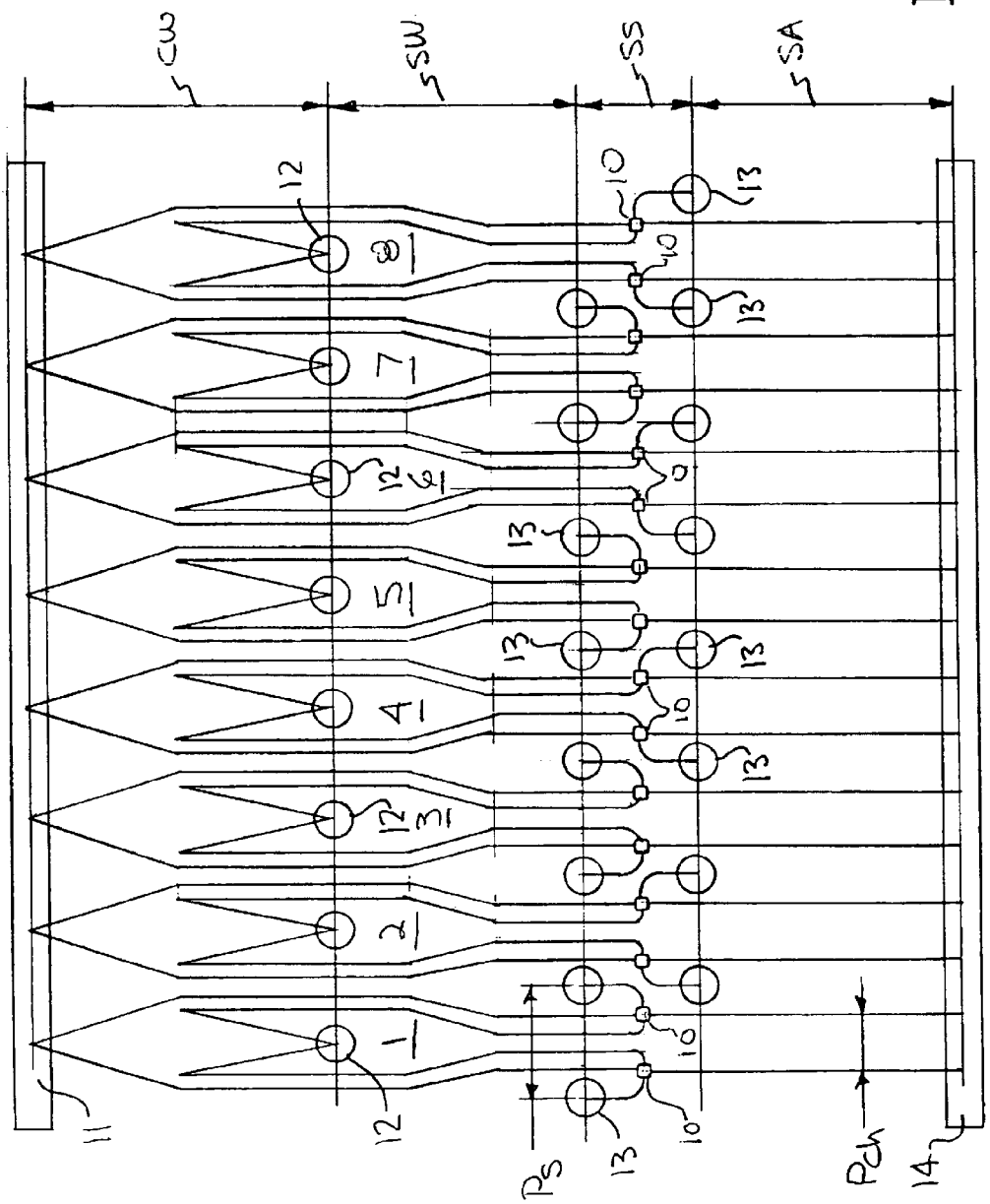

US 6,716,328 B1

MICROCHANNEL CROSS LOAD ARRAY WITH DENSE PARALLEL INPUT

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to loading of microchannel arrays, particularly to T or Cross (+) loading for microfluidic applications, and more particularly to an architecture for T or cross loading that enables a very dense layout of arrays of functionally identical shaped channels.

There are two main types of injection methods in microchannel electrophoresis. The first type is analogous to that used in discrete capillaries where the sample is introduced directly into the end of the microchannel, and there is one physical sample input port per channel. This has been used extensively, and is referred to as electrokinetic (ek) single port injection. The amount of sample actually injected into the column is a strong function of sample preparation, loading volume, input port shape and volume, exact loading placement, loading field and time, excess sample removal, holding time, etc. which may be hard to control.

The second type is a volumetric type of load called T load or Cross load, where the sample plug at the intersection of two microchannels is injected into the column. This type is exemplified by U.S. Pat. No. 5,900,130 issued May 4, 1999 to D. Benvegnu, et al. This load type is fundamentally controlled better by the geometry of the intersection, but now the number of input ports per channel has increased from one to three: sample, waste, and cathode. Ek effects may be present or used in the cross load, but the fundamental determinant of the amount of sample loaded and injected is the geometrical volume of the channel intersection, which is subsequently swept out by the running or separation field. The increased space required for additional input ports and the need to electrical bias all of them independently and initially fill them all with sieving media is geometrically and procedurally fraught with practical difficulties—especially for very high density arrays.

The present invention addresses these geometrical and practical operational difficulties. The invention provides an architecture or layout composition which enables a very dense layout of arrays of functionally identical shaped channels. The invention also simultaneously enables efficient parallel shapes and biasing of input wells, waste wells, and bias wells at the input end of the separation columns.

SUMMARY OF THE INVENTION

It is an object of the present invention to provide a microchannel cross load array with dense parallel input.

A further object of the invention is to provide a unique architecture for microchannel arrays using T or Cross loading for electrophoresis.

Another object of the invention is to provide a T or Cross loading architecture which enables a very dense layout of arrays of functionally identical shaped channels.

Another object of the invention is to provide an architecture for microfluidic configurations that simultaneously enables efficient parallel shapes and parallel biasing of the input wells, waste wells, and bias wells at the input end of microchannel separation columns.

Other objects and advantages of the present invention will become apparent from the following description and accompanying drawings. The present invention involves an architecture or layout composition for microchannel T or Cross (+) loading to enable dense parallel input for electrophoresis or other injection and separation chemistry experiments that are preformed in microfluidic configurations. The present invention is an architecture for microchannel arrays using T or Cross loading which solves prior problems associated with very high density arrays. The invention provides a way to layout a dense array of similar cross loaders so that high channel densities result, and a minimum member of access holes is used by sharing holes in the multiple channel layout. This invention uses unique geometrical pattern shaped channels and packing of the layout, taking advantage of several mirror symmetries in the layout, and enables the use of the Cross loader, such as described in about-referenced U.S. Pat. No. 5,900,130, in dense practical arrays. Based on this layout, experiments show that for the large microchannel array fabrication technology that is currently known, over 1000 channels can be formed on one plate. The architecture of this invention utilizes the Cross loader of the above-referenced patent which consists of two intersecting microchannels (four arms), and provides a package or layout of building blocks in a practical way for a very high density planar integrated array.

BRIEF DESCRIPTION OF THE DRAWINGS

The accompanying drawings, which are incorporated into and form a part of the disclosure, illustrate embodiments of the invention, and together with the description, serve to explain the principles of the invention.

FIGS. 1A and 1B illustrate the basic prior art Cross loaders.

FIGS. 2A, 2B, and 2C illustrate T and Cross loaders made in accordance with the present invention with FIG. 2A being generally similar to FIGS. 1A and 1B.

FIG. 3 illustrates an embodiment of a T load architecture of the present invention using circular holes with common rows.

DETAILED DESCRIPTION OF THE INVENTION

Figure 4:
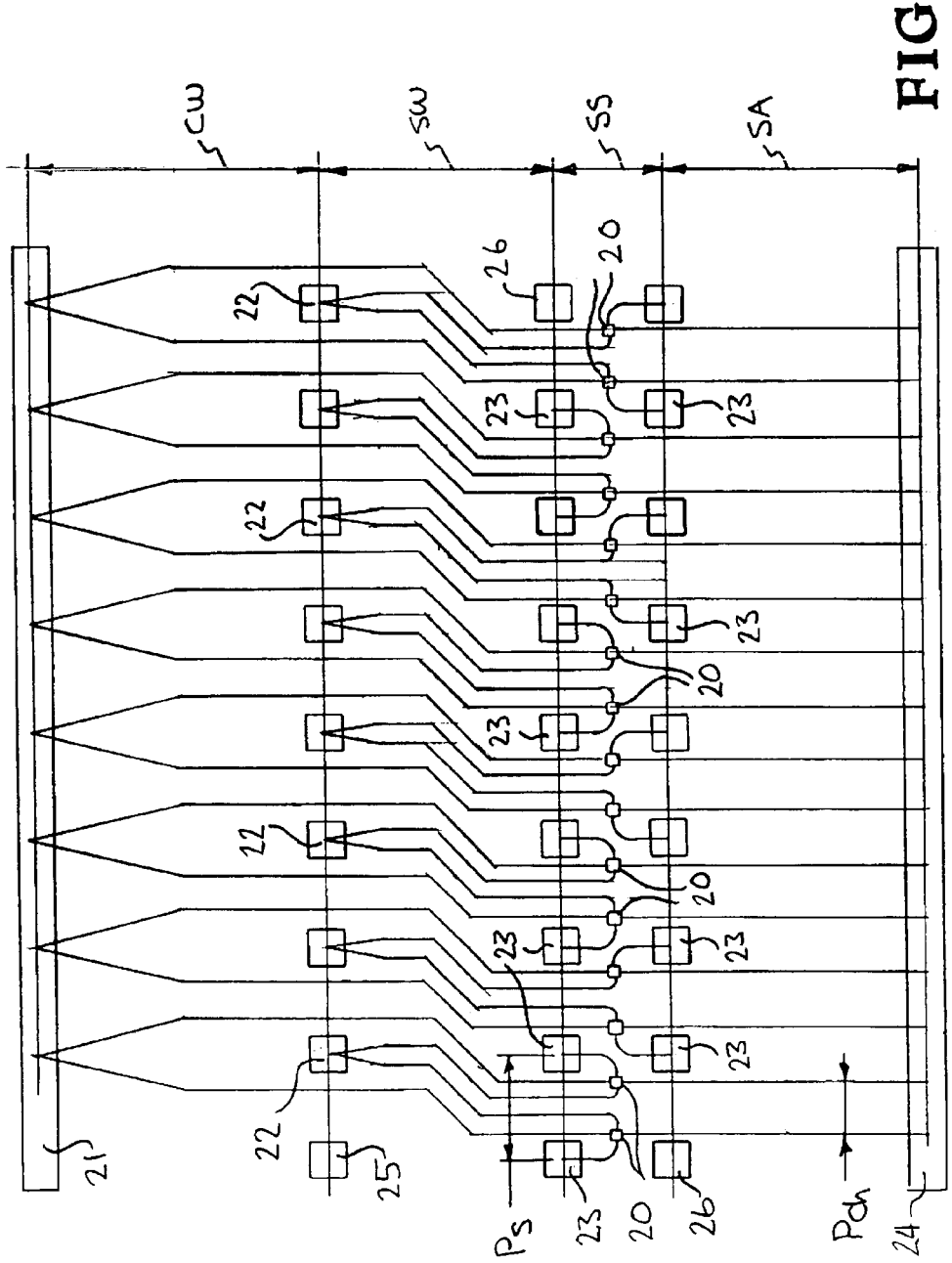
FIG. 4 illustrates an embodiment of a T load architecture of the present invention that enables the access hole array to be formed on a biaxial, collinear grid suitable for EDM machining (square holes), with common rows and columns.

The present invention provides an architecture for microchannel arrays using T or Cross loading which enables dense parallel inputs for electrophoresis or other microfluidic applications. The invention provides a way to layout a dense array of similar Cross loaders so that high channel densities result, and a minimum member of access holes is used by sharing holes in the multiple channel layout. The invention uses unique geometrical packing of the layout, taking advantage of several mirror symmetries in the layout. This architecture is a way to enable the use of the prior art Cross loader into dense practical arrays. An initial layout made in accordance with the present invention shows that for the large microchannel array fabrication technology that now exists, one could make over 1,000 channels on one plate. In addition, the present invention solves the problem of simultaneously enabling efficient parallel shapes and biasing of the input wells, waste wells, and bias wells at the input end of the separation columns.

Referring now to the drawings, FIGS. 1A and 1B illustrate the basic Cross load, such as described in above-referenced U.S. Pat. No. 5,900,130. When arrays of this type of layout are made, the configuration of the sample (S), waste (W), and cathode (C) input holes is very inconvenient or impractical for the external fluidic reservoirs and biasing electrodes, especially for very dense and large arrays; the dense intermixed ports require many separate fluidic seals and electrodes. Also, bending or differences in shape of the separation channel is very undesirable (resolution loss).

The key to this invention is the distortion of the fluidic path shapes and the changes in length, especially on the waste and cathode paths, and the use of multiple mirror image segments and the arrangement of the input ports so that the ports are arranged in common groups. With the common groups of input ports arranged in parallel rows, it becomes possible to access them with a few o-ring sealed reservoirs; this enables common excess fluid purging without cross contamination, and enables common electrical electrodes to be employed. This makes practical fill fixtures and loading apparatus possible; such can even be formatted to be consistent with the common titer array pitch density. This layout also enables the use of a common slot for the cathode (A) and anode (A) groups.

FIGS. 2A, 2B, and 2C illustrate the evolution of the geometric or architectural design of this invention in the transition from conventional layout (FIG. 2A) to the preferred layout of FIG. 2C. A key concept is to take separate portions of FIG. 2C and use both vertical and horizontal mirror images of those segments and to re-assemble them into arrays with rows and spacings that are compatible with input port fabrication and practical shaped fill reservoirs, such as shown in the embodiments of FIGS. 3 and 4.

Some of the key concepts of the present invention are:
1. Each electrode type is arranged in rows, so that the fluid reservoirs are easy to build.
2. The row arrangement allows a common bias electrode to be used, simplifying input loading fixtures.
3. The different flow channels and input structures have functionally identical shapes; thus being very important for uniform separation, filling, loading, injection, purging, refill, etc.
4. The architecture of the embodiment of FIG. 3 allows perfectly identical functional shapes. The holes may be square, round, or tapered.
5. The embodiment of FIG. 4 allows the waste holes to be colinear with the sample holes, i.e., in the same column, and thus in turn, enables fabrication by EDM machining or similar x-cut, y-cut machining for the mandrel; this allows very precise, small practical hole fabrication in very dense and large arrays. The holes may be square, round, or tapered.
6. Folded, nested waste path; equal in length to the cathode, if desired.
7. Short sample to cross path allowed (more thorough purging where it matters most, and quick load—ek or hydraulic pressure load).
8. Offset cross intersection allowed.
9. A minimum number of 1.5 holes per channel is needed.
10. The separation channels can be made straight (double output pitch) or virtually straight (single output pitch).
11. Sheath flow readout is enabled with a single or double plate cut at the anode (A) end.

FIG. 3 illustrates an embodiment of a Cross or T load architecture, similar to that shown in FIG. 2C, which uses circular holes or wells with common rows, but not columns; this allows the flow paths for each channel 1–8 to be identical in shape, using multiple mirror image pieces. The flow path from the Cross or T, indicated at 10, to the cathode 11 and to waste 12 are equal in length; the sample 13 to the cross 10 length is short compared to the other flow paths, but could be made much longer, or could have a junction offset for a bigger injection plug. Note that there is only one (1) waste hole 12 for each pair of channels. By way of example, the channel pitch, indicated by arrow Pch, is about 0.5–4.5 mm; and the sample pitch, indicated by arrow Ps is about 2Pch. The hole row spacing from cathode 11 to waste 12, indicated by arrow CW; from waste 12 to sample 13, indicated by arrow SW, and from sample 13 (first row) to sample 13 (second row), indicated by arrow SS, can be adjusted to accommodate load fixtures. The hole row spacing from sample 13 to anode 14, indicated by arrow SA, may be 2–500 mm. Each row has a common bias during operation. The cathode row 11 and distant anode row 14 are each common slots. The flow paths of each of channels 1 through 8 which extends from a sample hole 13 to the anode 14 holes as the number of sample holes. The cathode row 21 and distant anode row 24 are common slots. The holes 25 and 26 on the ends of the waste. row 12 and the sample rows 23, are formed in the EDM process (orthogonal rows and columns) but are not used. Other machining processes producing orthogonal rows and columns may be used (e.g., conventional NCM-1 feature at a time).

By way of example, sample holes 23 and excess holes 26 may have sides of a width in the range of 0.3 mm to 3 mm, waste holes 22 and excess hole 25 may have sides of a width in the range of 0.3 mm to 3 mm, cathode 21 may be a depth of 0.5 mm to 5 mm and width of 0.5 mm to 2 mm; and anode 24 may have a depth of 0.5 mm to 5 mm and width of 0.5 mm to 2 mm. Take flow paths 1–8, from injection points 20 to anode 24 may be a length of 2 mm to 500 mm; from injection points 20 to wastes 22 may have a length of 2 mm to 20 mm; from injection points 20 to cathode 21 may have a length of 2 mm to 20 mm; and from samples 23 to injection points 20 may have a length of 0.3 mm to 3 mm. The sample wells may be circular and waste wells may be square, but not by simple EDM process. A glass ultrasonic drill mandrel tool could be made with square bits and round bits on the same plate with far more effort and with less accuracy.

It has thus been shown that the present invention provides a geometry, architecture, topology, or layout composition for microchannel arrays using T or Cross loading for electrophoresis or other injection and separation chemistry experiments that are performed in microfluidic configurations. This architecture or geometry enables a very dense layout of arrays of functionally identical shaped channels. It also solves the problem of simultaneously enabling efficient parallel shapes and biasing of the input wells, waste wells and biasing wells at the input end of the separation columns. This invention establishes that for large microchannel array may have an overall length of 2 mm to 500 mm, for example, with the channels 1–8 having a width of 0.02 mm to 0.30 mm and depth of 0.02 mm to 0.15 mm. The sample holes 13, and waste holes 12 may have a diameter of 0.3 mm to 2 mm, with the common slots of cathodes 11 and anodes 14 having a width of 0.5 mm to 2 mm. While only sixteen (16) channels and associated sample hole, with only eight (8) waste holes have been illustrated for simplicity, numerous additional channels, etc. may be formed on the same plate, as pointed out above. The flow paths from the injection point to the cathode and from the injection point to the waste wells may be equal or unequal.

FIG. 4 illustrates an embodiment of a Cross or T load architecture of the present invention generally similar to FIG. 3, but which enables the access hole or well array to be formed on a biaxial, collinear grid suitable for Electric Discharge Machining (EDM) machining (square holes), with common rows and columns. In the scheme, the major difference is the input sample and waste holes are in common columns, rather than in staggered columns as in FIG. 3. The asymmetric flow paths from injection Cross or T 20 to cathode 21 and waste 22 can still be made the same lengths, just different shapes. The channel pitch, indicated by arrow Pch is about 0.5–4.5 mm; and the sample pitch, indicated by arrow Ps equals 2Pch, as in FIG. 3. The hole spacings from waste 22 to cathode 21, indicated by arrow CW; from waste 22 to a top row of sample 23, indicated by arrow SW; and from the top row of sample 23 to a lower row of sample 23, indicated by arrow SS, can be adjusted to accommodated load fixtures. The spacing from lower row of sample 23 to anode 24, indicated by arrow SA, is 2 mm to 500 mm, for example. Each row has a common bias during operation. Note that there are only half the number of waste fabrication technology, at least 1000 channels can be formed on one plate, thus providing a layout for a dense array of similar Cross or T loaders so that high channel densities result, and a minimum number of access holes are used by sharing holes in the multiple channel layout. The architecture of the present invention can be utilized for example, in capillary electrophoresis, chemical flow injection analysis, liquid chromatography, enhanced electrokinetic injection, chemical reaction micro capillary flow systems, combinatorial wet chemistry processing and analysis, microsample array preparation, etc. The architectural arrangement of this invention thus extends the use of T or Cross loads with the prior known problems associated with the use of such loads for dense parallel inputs. The sample and waste wells may have tapered walls for ease of sample needle/pipette array insertion.

While particular embodiments of the present invention have been illustrated and/or described, along with various parameters, etc., to exemplify and teach the principles of the invention, such are not intended to be limiting. Modifications and changes may become apparent to those skilled in the art, it is intended that the scope of the invention be limited only by the scope of the appended claims.

What is claimed is:

1. A microchannel Cross load array, comprising:
    a cathode,
    a anode,
    an array of at least two rows of sample wells arranged adjacent to but not overlapping said anode,
    an array of waste wells arranged along a common row and intermediate said at least two rows of sample wells and said cathode, and
    array of functionally identical channels, each channel having an injection point connected directly to only one well of said array of sample wells, connected directly to only one well of said array of waste wells, connected directly to said cathode and connected directly to said anode.

2. The microchannel Cross load array of claim 1, which said cathode and said anode each define common slots.

3. The microchannel Cross load array of claim 1, wherein said sample wells are selected from the group consisting of wells having substantially circular holes, wells having substantially tapered holes, and wells having holes.

4. The microchannel Cross load array of claim 1, wherein said waste wells define substantially circular holes.

5. The microchannel Cross load array of claim 1, wherein both said sample and waste wells define substantially circular holes.

6. The microchannel Cross load array of claim 1, wherein said sample wells define substantially square holes.

7. The microchannel Cross load array of claim 1, wherein said waste wells define substantially square holes.

8. The microchannel Cross load array of claim 1, wherein both said sample and waste wells define substantially square holes.

9. The microchannel Cross load array of claim 1, wherein both said sample and waste wells are formed on a biaxial, collinear grid by EDM machining or other machining process producing orthogonal rows and columns.

10. The microchannel Cross load array of claim 1, wherein said channels are identical in shape.

11. The microchannel Cross load array of claim 1, wherein said array of channels form flow paths for each channel which are identical in shape, using multiple mirror image pieces.

12. The microchannel cross load array of claim 1, wherein said array of channels form equal or unequal flow paths from said injection point to said cathode and from said injection point to said waste wells.

13. The microchannel Cross load array of claim 1, wherein said array of channels form symmetric flow paths from said injection point to said cathode and to said waste wells.

14. The microchannel Cross load array of claim 13, wherein said symmetric flow paths are of the same lengths.

15. The microchannel Cross load array of claim 1, wherein said array of sample wells are located in a plurality of rows.

16. The microchannel Cross load array of claim 15, wherein adjacent channels which are located adjacent said anode have a pitch, Pch, wherein adjacent sample wells in each row have as pitch, Ps, and wherein Ps equals 2Pch.

17. The microchannel Cross load array of claim 16, wherein the pitch, Pch, is about 0.5–4.5 mm.

18. The microchannel Cross load array of claim 15, wherein each row of sample wells has a common bias.

19. The microchannel Cross load array of claim 1, wherein said array of waste wells are located in a row, and have a common bias.

20. The microchannel Cross load array of claim 1, wherein said array of functionally identical channels comprises at least one pair of functionally identical channels.

21. The microchannel Cross load array of claim 1, wherein said array of functionally identical channels comprises a plurality of pairs of functionally identical channels.

22. The microchannel Cross load array of claim 21, wherein each of said plurality of pairs of functionally identical channel has a common waste well.

23. The microchannel Cross load array of claim 22, wherein said common waste well is positioned in alignment with at least one sample well.

24. The microchannel Cross load array of claim 22, wherein said common waste well is located in an offset position relative to at least one sample well.

25. The microchannel Cross load array of claim 22, wherein said common waste well is located from the injection point at about one-half the distance from the injection point to the cathode.

26. An architecture for microchannel arrays using T or Cross loading for injection and separation chemistry applications performed in microfluidic configurations,
    said architecture producing a dense layout of functionally identical shaped microchannels, sample wells, and waste wells, and including a common cathode and a common anode, said microchannels each having an injection point interconnecting a sample well, a waste well, a cathode and an anode, said microchannels each defining equal length flow paths between said injection point and said waste well, and between said injection point and said cathode.

27. The architecture for microchannel arrays of claim 26, wherein said flow paths are symmetric.

28. The architecture for microchannel arrays of claim 26, wherein said sample wells are located in a plurality of rows, and wherein said waste wells are located in a single row.

29. The architecture for microchannel arrays of claim 26, wherein said microchannels each include flow paths from said injection point to a sample well and from said injection point to said anode.

30. The architecture for microchannel arrays of claim 29, wherein adjacent flow paths of said channels located adjacent said anode have a channel pitch, Pch, wherein adjacent sample wells have a sample pitch, Ps, and wherein Ps=2Pch.

31. The architecture for microchannel arrays of claim 30, wherein the channel pitch, Pch, is about 0.5–4.5 mm.

32. The architecture for microchannel arrays of claim 26, wherein said sample wells and said waste wells having a configuration selected from the group consisting of circular and square shapes with straight or tapered walls.

33. The architecture for microchannel arrays of claim 26, wherein said common cathode and said common anode are each of a slot configuration.

34. The architecture for microchannel arrays of claim 26, wherein said sample wells are located in a plurality of rows, wherein said waste wells are located in a single row, and wherein each of said rows has a common bias.

35. A microchannel Cross load array, comprising:

a cathode, an array of sample wells, an array of waste wells, said sample wells comprising twice the number of waste wells, an anode, and an array of functionally identical channels, each channel having an injection point connected directly to only one well of said array of sample wells, connected directly to only one well of said array of waste wells, connected directly to said cathode and connected directly to said anode, each of said functionally identical channels has the same length from said injection point to said sample well, from said injection point to said waste well, from said injection point to said cathode, and from said injection point to said anode.

36. The microchannel Cross load array of claim 35, wherein said length from said injection point to said waste well is substantially the same as the length from said injection point to said cathode.

37. A microchannel Cross load array, comprising:

a cathode, an array of sample wells, an array of waste wells, said sample wells comprising twice the number of waste wells, an anode, and an array of functionally identical channels, each channel having an injection point connected directly to only one well of said array of sample wells, connected directly to only one well of said array of waste wells, connected directly to said cathode and connected directly to said anode, said array of functionally identical channels comprises a plurality of pairs of functionally identical channels, each of said plurality of pairs of functionally identical channels has a common waste well, said common waste well being located from said injection point at about one-half the distance from said injection point to said cathode.

38. The microchannel Cross load array of claim 37, wherein said common waste well is positioned in alignment with at least one sample well.

39. A microchannel Cross load array, comprising:

a cathode, an array of sample wells, an array of waste wells, said sample wells comprising twice the number of waste wells, an anode, and an array of functionally identical channels, each channel having an injection point connected directly to only one well of said array of sample wells, connected directly to only one well of said array of waste wells, connected directly to said cathode and connected directly to said anode, said array of functionally identical channels comprises a plurality of pairs of functionally identical channels, each of said plurality of pairs of functionally identical channels has a common waste well, said common waste well being located from said injection point at about the same distance from said injection point to said cathode.

40. The microchannel Cross load array of claim 39, wherein said common waste well is located in an offset position relative to at least one sample well.

41. A microchannel Cross load array, comprising:

a cathode, an array of sample wells, an array of waste wells, said sample wells comprising twice the number of waste wells, an anode, and an array of functionally identical channels, each channel having an injection point connected directly to only one well of said array of sample wells, connected directly to only one well of said array of waste wells, connected directly to said cathode and connected directly to said anode, said array of channels form flow paths from said injection point to said cathode and to said waste wells which are of the same lengths.

42. The microchannel Cross load array of claim 41, wherein said array of sample wells are located in a plurality of rows.

43. The microchannel Cross load array of claim 42, wherein adjacent channels which are located adjacent said anode have a pitch, Pch, wherein adjacent sample wells in each row have a pitch, Ps, and wherein Ps equals 2 Pch.

* * * * *